(12) United States Patent
Kadaba

(10) Patent No.: US 6,638,954 B2
(45) Date of Patent: Oct. 28, 2003

(54) Δ2-1,2,3-TRIAZOLINE ANTICONVULSANTS AND THEIR ACTIVE METABOLITE ANALOGUES, THE AMINOALKYLPYRIDINES, ARE EXCITATORY AMINO ACID ANTAGONISTS AND ANTIISCHEMIC AGENTS, USEFUL IN THE TREATMENT OF CEREBRAL ISCHEMIA RESULTING FROM STROKE

(75) Inventor: Pankaja K. Kadaba, Chadds Ford, PA (US)

(73) Assignee: K and K Biosciences, Inc., Chadds Ford, PA (US)

( * ) Notice: Subject to any disclaimer, the term of this patent is extended or adjusted under 35 U.S.C. 154(b) by 0 days.

(21) Appl. No.: 09/985,318

(22) Filed: Nov. 2, 2001

(65) Prior Publication Data

US 2002/0111371 A1 Aug. 15, 2002

Related U.S. Application Data

(60) Provisional application No. 60/307,360, filed on Jul. 25, 2001, and provisional application No. 60/244,930, filed on Nov. 2, 2000.

(51) Int. Cl.[7] .................... A61K 31/44; C07D 401/04
(52) U.S. Cl. ..................................... 514/340; 546/268.4
(58) Field of Search ........................ 514/340; 546/268.4

(56) References Cited

U.S. PATENT DOCUMENTS

| 4,511,572 A | 4/1985 | Kadaba |
|---|---|---|
| 4,618,681 A | 10/1986 | Kadaba |
| 4,689,334 A | 8/1987 | Kadaba |
| 4,820,721 A | 4/1989 | Kadaba |
| 5,648,369 A | 7/1997 | Kadaba |
| 6,083,964 A | 7/2000 | Kadaba |

*Primary Examiner*—Patricia L. Morris
(74) *Attorney, Agent, or Firm*—McDermott, Will & Emery

(57) ABSTRACT

Pharmaceutical compositions comprise as the active ingredient, nonneurotixic antiischemic compounds that are highly effective by the intraperitoneal route, and that are excitatory amino acid and NMDA/sigma receptor antagonists and are selected from the group consisting of those of the formulae,

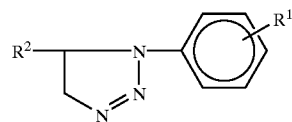

wherein $R^2$ is 4-pyridyl, 3-pyridyl, or 2-oxo-1-pyrrolidino and $R^1$ is 3,4- or 3,5-dichloro, p- or m-chloro, p- or m-bromo, p- or m-fluoro, p- or m-trifluoromethyl, p-methyl, p-methoxy, or hydrogen, and those of the formulae,

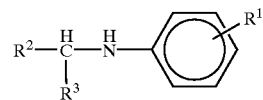

wherein $R_2$ is 4-pyridyl or 3-pyridyl, $R^3$ is hydrogen, methyl or ethyl and $R^1$ is 3,4- or 3,5-dichloro, p- or m-chloro, p- or m-bromo, p- or m-fluoro, p- or m-trifluoromethyl, p-methyl, p-methoxy or hydrogen.

31 Claims, No Drawings

Δ2-1,2,3-TRIAZOLINE ANTICONVULSANTS AND THEIR ACTIVE METABOLITE ANALOGUES, THE AMINOALKYLPYRIDINES, ARE EXCITATORY AMINO ACID ANTAGONISTS AND ANTIISCHEMIC AGENTS, USEFUL IN THE TREATMENT OF CEREBRAL ISCHEMIA RESULTING FROM STROKE

CROSS-REFERENCE TO RELATED APPLICATIONS

This application claims priority from Provisional Application Ser. No. 60/244,930, filed Nov. 2, 2000, and Provisional Application Ser. No. 60/307,360, filed Jul. 25, 2001, the disclosures of these provisional applications being incorporated herein by reference.

FIELD OF THE INVENTION

This invention relates to the drug potential of anticonvulsants in the treatment of stroke, particularly, several $\Delta^2$-1,2,3-triazoline and aminoalkylpyridine (AAP) anticonvulsants that seem to work by impairing the excitatory amino acid (EAA) L-glutamate (L-Glu) neurotransmission, as antiischemic agents, useful in the treatment of stroke victims.

There is strong evidence that the "excitotoxic" action resulting from the excessive accumulation of L-Glu plays a prominent role in human epilepsy as well as brain ischemia/stroke, leading to neuronal dysfunction and cell death. The 1,2,3-triazolines and the aminoalkylpyridine (AAP) metabolite analogues are two groups of novel anticonvulsants discovered in the Applicant's laboratories. These are very effective in the kindling and in the maximal electroshock (MES) seizure models of epilepsy, the best analogies to human partial seizures, where EAA neurotransmission plays an important role. Thus it is logical to expect that the anticonvulsant triazolines and AAP metabolite analogues would evince beneficial therapeutic potential in cerebral ischemia.

The ability of the triazolines and AAP compounds to afford protection and reduce neuronal degeneration are assessed in animal models of stroke, by utilizing the bilateral carotid occlusion model in the gerbil and the middle cerebral artery occlusion (MCAO) model in the rat. Post-ischemic gerbils undergo a predictable pattern of behavioral changes and the effects of drugs in producing alterations in this pattern are monitored by determining the post ischemic changes in locomotor activity as well as by changes in radial arm maze performance, and corroborated by post reperfusion histopathological assessment. In the MCAO rat model, a focal stroke model, drug effects are evaluated from their ability to reduce the infarct volume following MCAO.

BACKGROUND ART

There is a desperate need for clinically effective chemotherapeutic agents for intervention in and management of cerebral ischemia resulting from stroke. In the U.S. alone, 1.1 million individuals suffer stroke annually; it is the most common, and devastating neurological condition that kills more than a quarter million Americans every year and the leading cause of long-term intellectual and physical disability. In the past decade, it has become increasingly evident from data from numerous laboratories that EAA neurotransmission plays an important role in ischemic brain injury occurring in stroke and other neurological disorders (McCulloch, J., et al., Ed., "Frontiers in Pharmacology and Therapeutics: Excitatory Amino Acid Antagonists.", Oxford, UK; Blackwell Scientific Publishers, 287–326, 1991: Choi, D. W. & Rothman, S. M., Annu. Revs., Neurosci., 13, 171–182, 1991; Takagi, K., et al., J. Cereb. Blood Flow Metab., 13, 575–585, 1993; Graham, S. H., et al., J. Cereb. Blood Flow Metab., 13, 88–97, 1993; Muir, K. W., & Lees, K. R., Stroke, 26, 503–515, 1995). The excessive accumulation of the excitatory neurotransmitter L-Glu, followed by its excitotoxic action, has been strongly implicated in the cascade of pathological mechanisms that cause neuronal dysfunction and cell death in cerebral hypoxia-ischemia resulting from stroke, cardiac arrest, or mechanical brain injury. Thus, the EAA neurotransmitter systems may be considered potential therapeutic targets and development of agents that are EAA antagonists may constitute novel and effective therapies, as cytoprotective agents, in stroke.

SUMMARY OF THE INVENTION

It is accordingly one object of the present invention to provide novel $\Delta^2$-1,2,3-triazolines and AAP compounds and their method of preparation.

It is a further object of the present invention to provide antiischemic/antistroke agents which comprise triazolines and AAP compounds A further object of the present invention is to provide a method for the treatment of cerebral ischemia resulting from stroke, by administration of an effective amount of the triazoline and AAP compounds of this invention.

A further object of the present invention is to provide triazolines and AAPs bearing three different pyridyl substituents and a pyrrolidinone group, and methods for their use in the treatment of neurological disorders such as cerebral ischemia resulting from stroke and also in the treatment of epilepsy.

A still further object of the present invention is to provide triazolines and AAP compounds, as inhibitors of the EAA neurotransmitter L-glutamate. The triazolines and AAPs of this invention afford pronounced protection in the maximal electroshock seizure (MES) model in both mice and rats, by the intraperitoneal, intravenous, and oral route, which is indicative of their action as glutamate antagonists.

A still further object of the present invention is to provide antiischemic compositions that contain as the essential ingredient certain triazolines and AAPs and that are highly effective by the intraperitoneal and intravenous routes, the preferred routes of administration, in stroke victims, and use of these triazolines and AAPs as effective antiischemic drugs in the treatment of cerebral ischemia resulting from stroke.

Other objects and advantages of the present invention include use of the triazolines and AAPs in the treatment of stroke and epilepsy and also other neurological disorders such as Parkinson's disease, by virtue of their action as EAA antagonists and inhibitors of L-glutamate neurotransmission.

In satisfaction of the foregoing objects and advantages, there are provided by this invention several triazolines and AAPs which are useful as antiischemic/antistroke drugs. The various groups of triazolines and AAPs substituted with the various pyridyl groups and also the pyrrolidinyl group, may be characterized by the following general formulae:

(I)

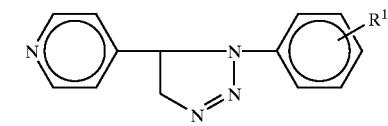

[1-(Phenyl)-5-(4-pyridyl)-Δ²-1,2,3-triazolines]

(II)

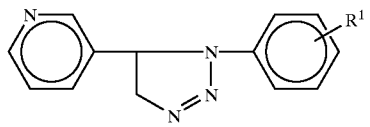

[1-(Phenyl)-5-(3-pyridyl)-Δ²-1,2,3-triazolines]

(III)

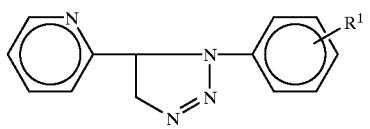

[1-(Phenyl)-5-(2-pyridyl)-Δ²-1,2,3-triazolines]

(IV)

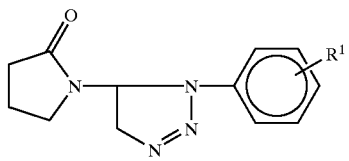

[1-(Phenyl)-5-(2-oxo-1-pyrrolidino)-Δ²-1,2,3-triazolines]

(V)

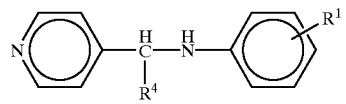

[1-(N-Phenyl)-1-(4-pyridyl)-1-ethylamine]
(propyl)

(VI)

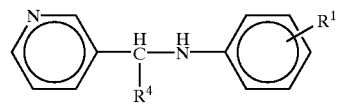

[1-(N-Phenyl)-1-(3-pyridyl)-1-ethylamine]
(propyl)

(VII)

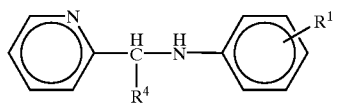

[1-(N-Phenyl)-1-(2-pyridyl)-1-ethylamine]
(propyl)

wherein $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen.

Also provided by this invention are non-toxic antiischemic compositions that are intraperitoneally and intravenously active and comprise as the active ingredient, a compound selected from those of the formulae (I–VII), wherein $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen.

Also provided are methods for the administration of the antiischemic compositions of this invention to mammals, including animals and humans, in the treatment of cerebral ischemia resulting from stroke, including both global ischemia and focal ischemia.

DESCRIPTION OF PREFERRED EMBODIMENTS

As indicated above, this invention relates to several groups of compounds belonging to the seven structures (I–VII) shown above, which are useful as antiischemic drugs in the treatment of cerebral ischemia resulting from stroke. In one group of triazolines (I) and AAPs (V), a 4-pyridyl substituent is present, in a second group of these compounds (II & VI), a 3-pyridyl substituent and in a third group (III & VII), a 2-pyridyl substituent is present. Also, in a fourth group of triazolines (IV), a 2-oxo-1-pyrrolidino group is present. In all three groups of AAP compounds, the $R^2$ group is methyl, ethyl or phenyl. The triazolines and AAPs of this invention are further substituted on the phenyl rings by 3,4- or 3,5-dichloro, p- or m-chloro, p- or m-bromo, p- or m-fluoro, p- or m-trifluoromethyl, p- or m-lower alkyl, p- or m-lower alkoxy or hydrogen. The triazolines and AAPs of this invention have potent antiischemic activity and protect the brain from neuronal damage in both global and focal ischemia, and are useful as antiischemic/antistroke drugs in the treatment of cerebral ischemia resulting from stroke in humans.

In one aspect of the present invention, three groups of triazolines and two groups of AAPs, are provided which have potent antiischemic activity and which have the general formulae represented by structures I, II and IV, and V and VI, respectively. In the above formulae, in structures I and II, the 5-substituent is 4-pyridyl or 3-pyridyl and $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen. In structure IV, the 5-substituent is a 2-oxo-1-pyrrolidino group and $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen. Structures V and VI, are 4-pyridyl and 3-pyridyl AAPs respectively, where $R^4$ is methyl, ethyl or phenyl and $R^1$ is 3,4- or 3,5-dichloro, p- or m-chloro, p- or m-bromo, p- or m-fluoro, p- or m-trifluoromethyl, p- or m-lower alkyl, p- or m-lower alkoxy, or hydrogen. Several of these triazolines and AAP compounds are potent anticonvulsants and are already under U.S. patent protection (P. K. Kadaba, U.S. Pat. No. 4,511, 572, 1985; U.S. Pat. No. 4,689,334, 1987; U.S. Pat. No. 4,820,721, 1989; U.S. Pat. No. 5,648,369, 1997; U.S. Pat. No. 6,083,964, 2000).

In a second aspect of this invention, there are provided novel antiischemic compositions which are effective by the intraperitoneal and intravenous routes and are non-toxic, and which comprise as the active ingredient an effective amount of a compound selected from those of the seven groups represented by structures (I–VII), and having 4- or 3-pyridyl, or 2-oxo-1-pyrrolidinyl substituent groups, and $R^4$ and $R^1$ are as described above.

There are further provided by this invention, methods for the administration of the antiischemic compositions to mammals including animals and humans.

In a third aspect of this invention, there are provided triazoline and AAP compounds of the formulae represented by the structures (I–VII), and which exhibit pronounced and selective activity in the MES test and the kindling model of epilepsy, and are useful in the treatment of stroke.

Significance of Pronounced Selective Activity in the MES Test:

Both the triazolines and the AAP compounds of this invention exhibit pronounced and selective anticonvulsant activity in the maximal electroshock seizure (MES) test. While the triazolines show activity in the subcutaneous Metrazole (scMet) test also, the AAPs show hardly any activity in the scMet test. The activity of the compounds of this invention in the MES test is of great significance, because partial seizures in humans correlate positively with experimental seizures elicited by the MES test [Porter, R. J. and Pitlick, W. H., In "Basic and Clinical Pharmacology", 4th Edn., B. G. Katzung Ed., Appleton & Lange, C. A., 1989, pp 287–303]. Since antiepileptic drugs effective against MES seizures alter ionic transport across excitable membranes, the triazolines and the AAPs that evince significant activity in the MES test, may be expected to attenuate EAA neurotransmission. There is strong evidence that the excitatory neurotransmitter glutamate plays a key role in EAA neurotransmission along limbic circuits which are particularly relevant to kindling epileptogenesis. Since the triazolines and the AAPs are quite effective in the kindling model, both these classes of compounds could be expected to be effective glutamate antagonists.

1.2.3-Triazoline and AAP Anticonvulsants and Their Mechanism of Anticonvulsant Activity, as Inhibitors of Both Post-and Presynaptic EAA Neurotransmission:

Previous studies in our laboratories had led to the emergence of the 1,2,3-triazoline heterocycles represented by structures I–IV, as a new class of anticonvulsant agents with a unique mechanism of action quite different from the more traditional anticonvulsants (Kadaba, P. K., J. Med. Chem., 31, 196–302, 1988; "Drugs of the Future", 15, 1013–1024, 1990; Kadaba, P. K., and Slevin, J. T., Epilepsia, 29, 330, 1988; Kadaba, P. K., and Slevin, J. T., Pharmaceut. Res., 6, S-42, 1989; Kadaba, P. K. and Slevin, J. T., 200th Nat. Meeting of the ACS, Washington, D.C., Abstracts, 56, MEDI 31, 1990; Kadaba, P. K., Stevenson, P. J., Nnane, I. P., and Damani, L. A., Bioorg. Med. Chem., 4, 165–178, 1996). The triazolines afford a high degree of protection in seizure provocation by chemical (scMet) and electrical (MES) stimuli and have good protective indices. They offer complete protection against N-methyl D-aspartate (NMDA)-induced seizures in the mouse at significantly low $ED_{50}$ values: (Kadaba, P. K., et al., Bioorg. Med. Chem., 4, 165–178, 1996). They show good response on oral administration and a good margin of safety. They compare very well with prototype antiepileptic drugs in both mice and rats. Unlike the prototype drugs, one triazoline represented by structure I, $R^1$=p–Cl, offers complete protection against stimulus-induced electrographic after-discharge seizures and generalized convulsions, in both amygdala-kindled ($ED_{50}$=215±61 mg/kg) and entorhinal-kindled rats ($ED_{50}$= 423±45 mg/kg), in non-sedative, non-neurotoxic doses (Kadaba, P. K., "Drugs of the Future", 15, 1013–1024, 1990: Kadaba, P. K. & Slevin, J. T., Pharmaceut. Res., 6, S-42, 1989).

Studies on the metabolism and in vivo and in vitro pharmacology of triazolines represented by structure I and potential metabolites, seem to indicate that the triazolines may be functioning as prodrugs and act by a unique "dual-action" mechanism; while the parent triazoline inhibits the presynaptic release of glutamate (58% at 50 µM and 83% at 100 µM drug concentration), the active B-amino alcohol metabolite displaces >90% of the binding of [$^3$H]-Glu from glutamate receptors, and 56% of the binding of [$^3$H]MK-801, from the MK-801 sites on the NMDA receptor ionophore complex (Kadaba, P. K., ACS Abstrs. MEDI 144, 1991; Kadaba, P. K. & Slevin, J. T., Epilepsia, 29, 330, 1988; Pharmaceut. Res., 6, S-42, 1989; ACS Abstrs., 56, MEDI 31, 1990; Kadaba, P. K., et al., Bioorg. Med. Chem. 4, 165–178, 1996). Furthermore, radioligand binding studies at ion-channel binding sites using [$^3$H]TBOB, indicates significant activity at Cl$^-$ channels ranging from 50 to 63% at 10 µM concentration, for triazolines belonging to structure I (Kadaba, P. K., et al., Bioorg. Med. Chem. 4, 165–178, 1996). Augmentation in Cl$^-$ influx is a useful membrane action that reduces membrane excitability or alters circuit behavior to favor inhibition, and thus might help suppress the firing of glutamatergic neurons and hence glutamate release. Such drugs may be most beneficial in the control of prolonged seizures such as in status epilepticus where excessive neuronal firing occurs (Choi, D. W., Cerebrovasc. Brain Metab. Revs., 2, 105–147, 1990). And indeed, the complete protection afforded by triazoline I ($R^1$=p–Cl) against amygdala- and entorhinal-kindled seizures as well as NMDA-induced convulsions is significant, in view of the current concepts regarding the central role of EAA neurotransmission, particularly L-Glu, in the kindling model of human partial epilepsy.

Studies by the Applicant on the metabolism and pharmacology of the triazoline anticonvulsants have led to the evolution and discovery of the aminoalkylpyridines (AAPs) as a unique class of orally active anticonvulsant agents, superior to the triazolines themselves (Kadaba, P. K., et al., Bioorg. Med. Chem., 2, 165–178, 1996; Kadaba, P. K., U.S. Pat. No. 4,511,572, 1985; U.S. Pat. No. 4,618,681, 1986; U.S. Pat. No. 4,689,334, 1987; U.S. Pat. No. 4,820,721, 1981). Work on the aminoalkylpyridines indicate they are non-toxic, and highly effective by the oral route, with protective indices greater than 20. The AAPs also show high anticonvulsant activity in the MES test and are practically inactive in the scMet test (Deshmukh, T. R. & Kadaba, P. K., Med. Chem. Res., 3, 223–232, 1993; U.S. Pat. No. 5,648, 369,1997).

Radioligand binding and release studies indicate that the ability of triazolines to impair presynaptic release of glutamate is retained to the full extent or better in the corresponding AAP compounds (V, $R^1$=p–Cl) (74% at 50 µM and 80% at 100 µM drug concentration as also the postsynaptic activity of the β-amino alcohol, albeit at a different site; the AAP compounds weakly displace [$^3$H] DTG, a o specific ligand, with Ki values in the µM range and show no affinity for the PCP sites (Kadaba, P. K., ACS Abstrs. MEDI 073, 1992; Pharmaceut. Res., MNPC 5013, 11, S-120, 1994a; Epilepsia, AES, Dec. 5, 1994b; Deshmukh, T. R., & Kadaba, P. K., J. Pharm. Res. 9, S-109, 1992; Med. Chem. Res. 3, 323, 1993; Kadaba, P. K., & Deshmukh, T. R., ACS Abstrs., MEDI, 1069, 1993a; Amino Acios, June, 1993b; Kadaba, P. K., et al., Bioorg. Med. Chem., 2, 165–178, 1996). As o and PCP sites are two distinct molecular entities (Kamenka, J. M. & Domino, E. F., (Eds), "Multiple Sigma and PCP Receptor Ligands: Mechanisms for Neuromodulation and Neuroprotection?", NPP Books, P.O. Box 1491, Ann Arbor, Mich., 48106, 1992) and the o receptor is not a component of the NMDA receptor-ionophore complex, the potent anticonvulsant activity of the AAPs seems to result from their selective low-affinity interaction at $o_1$ sites. The selectivity of the AAPs for the o receptor sites with no activity at the PCP sites, might also account for the absence of undesirable toxic side effects in these compounds.

EAA Neurotransmitter Systems and the NMDA Receptor Complex in Relation to Epilepsy and Cerebral Ischemia:

The role of EAAs and the NMDA receptor in health and disease are extensively reviewed (Cavalheiro, E. A., Lehmann, J., and Turski, L., Eds., "Frontiers in Excitatory Amino Acid Research", A. R. Liss, New York, N.Y., 1988; Cotman, C. W., Bridges, R. J., Taube, J. S., Clark, A. S., Geddes, J. W., and Monaghan, D. T., *J.NIH Res.*, 1, 65, 1989; Dingledine, R., Boland, L. M., Chamberlin, N. L., Kawasaki, K., Kleckner, N. W., Traynelis, S. F., and Verdoom, T. A., *CRC Crit. Rev. Neurobiol.*, 4, 1, 1988; Honore, T., *Med Res. Rev.* 9, 1, 1989; Johnson, G., *Ann. Rep. Med. Chem.*, 24, 41, 1989). Overstimulation of the NMDA receptor by high levels of glutamate has been implicated in both epilepsy (Cavalheiro, E. A., Lehmann, J., and Turski, L., Eds., "Frontiers in Excitatory Amino Acid Research", A. R. Liss, New York, N.Y., 1988; Fisher, R. S. and Coyle, J. T., Eds., "Neurotransmitters and Epilepsy", Wiley-Liss, New York, N.Y., 1991) and stroke (Meldrum, B. S. and Garthwaite, J., *TIPS*, 11, 379–385, 1990; Rothman, S. M. and Olney, J. W., *Ann. Neurol.*, 19, 105–111, 1986). Both diseases have been suggested to have a common pathology, i.e., chronic or acute cell death resulting from EAA-induced "excitotoxicity" (Greenamyre, J. T., Maragos, W. F., Albin, R. L., Penny, J. B., and Young, A. B., *Prog. Neuro Psychopharmacol & Biol. Psychiat.*, 12, 421, 1988; Mayer, M. L., and Westbrook, G. L., *Prog. Neurobiol.*, 28, 197, 1987; Choi, D. S., *Neuron*, 1, 623, 1988; Simpson, M. D. C., Royston, M. C., Deakin, J. F. W., Cross, A. J., Mann, D. M. A., and Slater, P., *Brain Res.*, 462, 76, 1988). Excessive accumulation of glutamate leads to overactivation of the NMDA receptor resulting in excessive intraneuronal $Ca^{2+}$ which precipitates neurodegeneration and neuronal death (Cotman, C. W., Bridges, R. J., Taube, J. S., Clark, A. S., Geddes, J. W., and Monaghan, D. T., *J. NIH Res.*, 1, 65, 1989). Evidence for the excitotoxic action of glutamate at the NMDA receptor, derived from numerous studies of cultured cortical neurons in vitro (Choi, D. S., *Neuron*, 1, 623, 1988), suggests an influx of $Ca^{2+}$ through the stimulated NMDA ionophore to be a prerequisite for cell death to occur (Choi, D. S., *Neuron*, 1, 623, 1988; Hahn, J. S., Aizenman, E., and Lipton, S. A., *Proc. Natl. Acad. Sci.*, 85, 6556, 1988; Ogura, A., Miyamoto, M. and Kudo, Y., *Exp. Brain Res.* 73, 447, 1988). Agents that block the action of glutamate and thus the overstimulation of the NMDA receptor thus represent novel therapies, as neuroprotective agents, for both epilepsy and cerebral ischemia resulting from stroke (Johnson, G., *Ann. Rep. Med. Chem.*, 24, 41, 1989; Cotman, C. W., Bridges, R. J., Taube, J. S., Clark, A. S., Geddes, J. W., and Monaghan, D. T., *J. NIH Res.*, 1, 65, 1989). Thus, based on the ability of the triazoline and the AAP anticonvulsants to effectively impair glutamate neurotransmission, it appears logical to expect that these compounds would provide beneficial drug candidates for stroke-related ischemic brain damage.

EAAs and the Kindling Model of Epilepsy:

The kindling phenomenon mimics human epilepsy (Kalichman, M. W., *Neurosci. Biobehav. Rev.*, 6, 165, 1982) and there is increasing evidence that EAAs may play an important role in kindling mechanisms. EAAs may be critically involved in both epileptogenesis and as a focus for the mechanism of action of anticonvulsants (Meldrum, B. S., and Chapman, A. G., In "Glutamine, Glutamate, and GABA in the Central Nervous System,", L. Hertz, et al., Ed., Alan R. Liss, Inc., New York, 1983, pp 625–641; Cavalheiro, E. A., Lehmann, J., and Turski, L., Eds., "Frontiers in Excitatory Amino Acid Research", A. R. Liss, New York, N.Y., 1988; Muir, K. W. and Lees, K. R., *Stroke*, 26, 503–513, 1995). Enhanced activity at the EAA synapse will lower the threshold and promote hyperactivity of the postsynaptic neuron. Evidence for a causal connection between EAA release and onset of hyperactivity has been provided by the use of specific EAA receptor antagonists, APB, APV, and APH, in various models of epilepsy (Cruczwar, S. J., and Meldrum, B. S., *Eur. J. Pharmacol.*, 83, 335, 1982).

EAAs and Cerebral Ischemia:

Brain regions such as the hippocampus and the dorsolateral striatum that are enriched in EAA receptors are especially vulnerable to ischemic lesions (Jorgensen, M. D. and Diemer, N. A., *Acta Neurol. Scand.*, 66, 536–46, 1982) and selective brain lesioning studies have supported a role for glutamate in ischemic and hypoglycemic brain injury (Jorgensen, M. B., Johnson, F. F., and Diemer, N. H., *Acta Neuropathol.*, 73, 189, 1987; Linden, T., Kalimo, H., and Weiloch, T., *Acta Neuropathol.*, 74, 335, 1988). Furthermore, ischemia-induced hippocampal damage is reduced by prior local infusion of EAA receptor antagonists (Simon, R. P., Griffiths, T., Evans, M. C., Swan, J. H., and Meldrum, B. S., *J. Cereb. Blood Flow Metab.*, 4, 350–361, 1984; Simon, R. P., Swan, J. H., Griffiths, T., and Meldrum, B. S., *Science*, 226, 850–852, 1984) or by their systemic administration (Boast, C. A., Gerhardt, S. C., Pastor, G., Lelunann, J., Etienne, P. E., and Liebman, J. M., *Brain Res.*, 442, 345–348, 1988). Glutamate can trigger toxic neuronal degeneration with considerable potency and speed; a 5-minute exposure to 100 $\mu$M Glu is sufficient to destroy large numbers of cultured cortical neurons (Choi, D. W., Maulucci-Gedde, M. A., Kriegstein, A. R., *J. Neurosci.*, 7, 357–368, 1987). Such brief intense exposure likely accompanies several types of acute insults, including hypoxia (Rothman, S. M., *J. Neurosci.*, 4, 188–191, 1984), ischemia (Simon, R. P., Griffiths, T., Evans, M. C., Swan, J. H., and Meldrum, B. S., *J. Cereb. Blood Flow Metab.*, 4, 350–361, 1984; Simon, R. P., Swan, J. H., Griffiths, T., and Meldrum, B. S., *Science*, 226, 850–852, 1984) and prolonged seizures (Ben-Ari, Y., *Neuroscience*, 14, 375–403, 1985).

In the hippocampus, the pattern of neuronal loss is similar after an episode of ischemia or of status epilepticus or temporal lobe epilepsy, the most common form of focal (partial) epilepsy. Irreversible cell loss is common in the hilus of the hippocampal area dentata and in the CA1 and CA3 pyramidal cell layers. Prolonged (24 hours) electrical stimulation of the perforant path fibers in vivo produces histopathological changes in the hippocampal CA1 and CA3 pyramidal neurons similar to those elicited by EAAs (Meldrum, B. S., and Corsellis, J. A. N., In "Greenfield's Neuropathology", 4th Edn., J. H. Adams, et al., Ed., 1984, pp 921–950; Sloviter, R. S., *Brain Res. Bull.*, 10, 675–697, 1983; Sloviter, R. S., *Science*, 73, 1987). The increased activity in excitatory hippocampal pathways is suggested as the cause for the irreversible damages to cells, probably by the release of EAAs in neurotoxic concentrations followed by $Ca^{2+}$ influx through the stimulated NMDA receptor-ion channel complex. The mitochondria in selectively vulnerable hippocampal neurons show massive overloading with $Ca^{2+}$ during status epilepticus and after 2 hours of reperfusion following cerebral ischemia (Griffiths. T., *Neuroscience*, 10, 385–395, 1983).

The compounds of the present invention are useful in pharmaceutical compositions using conventional pharmaceutical carriers or vehicles for administration to humans and animals in unit dosage forms, such as tablets, capsules, pills, powders, granules, suppositories, sterile parenteral solutions or suspensions, sterile non-parenteral solutions or suspensions, oral solutions or suspensions, oil in water or water in oil emulsions and the like, containing suitable quantities of the active ingredient.

Compositions for injection, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder form for reconstitution at the time of delivery with a suitable vehicle, such as sterile water. In injectable compositions, the carrier is typically comprised of sterile water, saline or another injectable liquid. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, and the particular compound selected. Such matters, however, are left to the routine discretion of the physician according to principles of treatment well known in the medical arts. The compositions of this invention for human delivery per unit dosage, whether liquid or solid, comprise from about 0.01% to as high as about 99% of the active compound, the preferred range being from about 10–60%.

The invention described herein also includes a method of treating a mammal in need of ischemia treatment comprising administering to said mammal the claimed composition in an amount effective to treat said condition. About 1 to 300 mg/kg of body weight, preferably about 25 to 200 mg/kg, one to four times daily is preferred.

The 5-pyridyl substituted triazoline compounds represented by structures I, II and III of this invention may be prepared by the reaction of diazomethane with Schiff bases as described in the Applicant's previous patents on triazolines (P. K. Kadaba, U.S. Pat. No. 4,511,572, 1985; U.S. Pat. No. 4,689,334, 1987, the disclosures of which are hereby incorporated by reference), and illustrated in Equation 1.

Equation 1

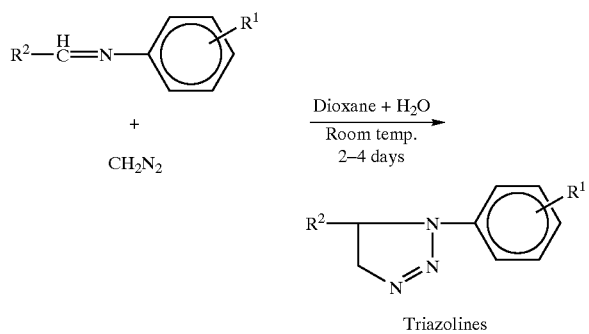

Triazolines where $R^2$ is 4-, 3- or 2-pyridyl and $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen.

In the method of preparation, the reaction between the Schiff base and diazomethane is carried out by treating the appropriate Schiff base with a dioxane solution of diazomethane at room temperature, as described previously (P. K. Kadaba, U.S. Pat. No. 4,511,572, 1985; U.S. Pat. No. 4,689,334, 1987).

The following examples are presented to illustrate the invention, but it is not to be considered as limited thereto. In the examples and throughout the specifications, parts are by weight unless otherwise indicated.

EXAMPLE 1

Preparation of 1-Phenyl-5-(4-,3-, or 2-pyridyl)-1,2,3-triazolines:

To a wet (undried) solution of diazomethane in p-dioxane (0.06 mole), contained in an Earlenmeyer flask and kept cold in an ice bath, is added the Schiff base (0.03 mole), and gently swirled until complete solution resulted. The flask is then stoppered with a clean cork, and allowed to stand at room temperature for 24–96 hours as necessary. At the end of the reaction, if crystals of the triazoline have appeared, the reaction mixture is filtered, and the filtrate cooled and diluted with water until a precipitate is obtained. It is filtered, and crystallized from ethanol or acetone or acetone-petroleum ether. The total yield of pure products ranges from 60–80%.

The 1,2,3-triazolines that are prepared according to the above described procedure are all patented (P. K. Kadaba, U.S. Pat. No. 4,511,572, 1985; U.S. Pat. No. 4,689,334, 1987) and presented in Table I along with their melting points and yields.

The 5-(2-oxo-1-pyrrolidino)-1,2,3-triazolines represented by structure IV of this invention, may be prepared by reacting aryl azides with N-vinylpyrrolidinone as described in the U.S. Patent (P. K. Kadaba, U.S. Pat. No. 4,820,721, 1989, the disclosure of which is hereby incorporated by reference), and shown in Equation 2.

Equation 2

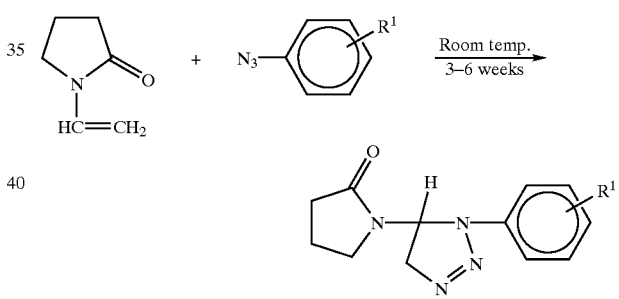

where $R^1$ is as defined above.

In the method of preparation, the reaction between the N-vinylpyrrolidinone and the phenyl azide is carried out at room temperature in ethanol as solvent, and allowed to stand in the dark for several weeks, depending on the reactivity of the phenyl azides. Refluxing the reaction mixture eliminates the 5-(2-oxo-1-pyrrolidino) group and yields the 1-phenyl triazole.

The following examples are presented to illustrate the invention, but it is not to be considered as limited thereto. In the examples and throughout the specifications, parts are by weight unless otherwise indicated.

EXAMPLE 2

Preparation of 1-Phenyl-5-(2-oxo-1-pyrrolidino)-$\Delta^2$-1,2,3-triazolines

To the N-vinylpyrrolidinone is added the appropriately substituted phenyl azide, and the reaction mixture is allowed to stand in the dark at room temperature, with periodic shaking, for several weeks, depending on the reactivity of the azide. The reaction is considered to be complete when the oily mixture has almost solidified to a crystalline mass.

The chunky mass of crystals is triturated with small portions of ethanol, suction filtered and washed several times with ether or an ether-petroleum ether mixture, as the case may be, until all of the unreacted N-vinylpyrrolidinone is removed. The triazolines are crystallized from acetone or acetone-petroleum ether mixture. The yields of the pure compounds range from 45% to 75%.

The 1-phenyl-5-(2-oxo-1-pyrrolidino)-1,2,3-triazolines prepared according to the above procedure are patented (P. K. Kadaba, U.S. Pat. No. 4,820,721,1989) and are given in Table II along with their melting points and yields.

The aminoalkylpyidines of this invention, represented by structures V, VI and VII, may be prepared by the reaction of pyridyl alkyl ketones with the appropriate anilines, followed by sodium borohydride reduction of the resulting ketimines, according to Equation 3, following the procedure described in an earlier patent (P. K. Kadaba, U.S. Pat. No. 5,648,369, 1997, the disclosure of which is hereby incorporated by reference).

Equation 3

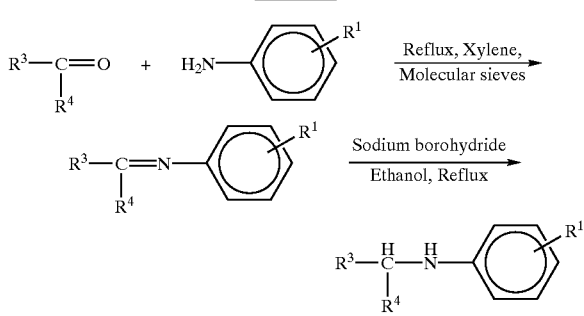

In the above equation, $R^3$ is 4-, 3- or 2-pyridyl group, $R^4$ is methyl or ethyl and $R^1$ is as defined above previously.

In the method of preparation, the pyridyl alkyl ketone is condensed with the aniline in refluxing xylene, in the presence of commercially available molecular sieves. The imine formed by this reaction is then reduced by sodium borohydride in ethanol.

The following examples are presented to illustrate the invention, but it is not to be considered as limited thereto. In the examples and throughout the specifications, parts are by weight unless otherwise indicated.

EXAMPLE 3

Preparation of 1-[N-(Phenyl)-1-(4-, 3-, or 2-pyridyl)]-1 ethyl (or propyl) amine:

A mixture of the appropriately substituted acetyl or propionyl pyridine (0.06 mole) and the appropriately substituted aniline (0.06 mole) in xylene (150 ml) is refluxed for 4 hours in the presence of molecular sieves (75 g; Davison, grade 514, effective pore size 4 A°, 8–12 mesh beads). At the end of the reaction, the molecular sieves are filtered, washed with benzene and the combined filtrates rotary evaporated to remove xylene. The syrupy residual material is crystallized from benzene or benzene-petroleum ether mixture to yield the pure imines in yields varying from 40% to 60%. The imines that are prepared according to this procedure are given in Table III, along with their yields and melting points.

Sodium Borohydride Reduction of Imines:

To a solution of the imine (0.03 mol) in ethanol (100 ml), is added finely powdered sodium borohydride (0.15 mol) and the reaction mixture refluxed with magnetic stirring for 2–4 hours.

The reaction mixture is then cooled in an ice bath and the excess sodium borohydride is destroyed by slow addition of dilute hydrochloric acid (1:1 mixture), until the reaction mixture is acidic and no more hydrogen evolution is noticed. The white inorganic solids that precipitate are dissolved by addition of water and the solution then made basic with sodium hydroxide. It is then cooled in the refrigerator for 1–2 days, when the 1-[N-(phenyl)]-1-(pyridyl)-1-alkylamines appear as white to beige colored solids. They are filtered, washed well with water until the filtrate is neutral, and recrystallized from a mixture of acetone-petroleum ether or tertiarybutyl methyl ether and petroleum ether. In Table IV, melting points and yields are given for all the 1-[N-(phenyl)]-1-(pyridyl)-1-ethyl- (or propyl) amine compounds that are prepared, including a number of new compounds, not known before.

EXAMPLE 4

The 1,2,3-triazolines and the AAP compounds of this invention are effective by the intraperitoneal, intravenous, and oral routes of administration. These compounds are effective antiischemic/antistroke agents that are useful in the treatment of cerebral ischemia in humans, both focal and global, resulting from stroke.

The potency of these compounds range from those which are very highly potent to those of good medium potency, with no accompanying toxicity, in both the gerbil model of global ischemia and the rat model of focal ischemia.

There is a definite need for more effective, clinically useful drugs in the management of stroke. Lipophilicity and penetration of the blood brain barrier are important factors to be taken into consideration when designing antistroke drugs, because systemic drug administration as quickly as possible after an episode of stroke is essential to prevent the onset and spread of neuronal injury. The highly lipophilic triazolines and AAPs can enter the brain in less than 15 minutes after intraperitoneal administration, and reduce or prevent excitotoxicity as early as possible in the ischeimic brain. Furthermore, their oral activity, especially that of the AAPs, makes them suitable candidates for delayed post treatment of the stroke victims, without evincing undue motor toxicity.

Evaluation of Antiischemic Activity:

A series of triazolines with different 5-substituents and the corresponding metabolite analogue compounds, the AAPs, of this invention, has been evaluated for antiischemic activity by the intraperitoneal route using two reliable paradigms of brain injury in stroke, the bilateral carotid occlusion model in the gerbil and the middle cerebral artery occlusion (MCAO) model in the rat. These two experimental procedures will indicate the potential of the anticonvulsant triazolines and AAPs, for reducing or preventing neuronal damage following cerebral ischemia.

The compounds are initially tested in the gerbil model of global ischemia, to establish the presence or absence of neuroprotective effect in the drug, when administered intraperitoneally as a pretreatment compound. Compound's ability to protect neurons from reperfusion injury in the gerbil is carried out using histopathological and behavioral assessments. The more active compounds are then advanced for further evaluation in the rat MCAO model of reversible focal cerebral ischemia after ip administration. This model is a clinically relevant model, as it mimics stroke in humans. Compound evaluation in the rat model consists of behavioral and histopathological studies and focused on hippocampal damage in the CA1 and CA3 pyramidal neurons.

EXAMPLE 5

The Bilateral Carotid Occlusion Model of Global Ischemia in the Gerbil to Study the Effects of Pretreatment Doses.

Male gerbils (50–60 gm, Tumblebrook Farm, West Brookfield, Mass.) are housed in groups of three for at least one week prior to instrumentation. Following surgery, the gerbils are singly housed in order to avoid the possible accidental induction of ischemia by cage mates. Food and water are available ad libitum in the home cage. All gerbils are maintained under a 12 hr light/dark cycle.

Transient ischemia is produced by occluding both common carotids using surgically placed occluders (Chandler, M. J., et al., *J. Pharmacol. Meth* 14, 137–146, 1985). A ventral midline incision is made in the neck of gerbils anesthetized with pentobarbital (40 mg/kg). Common carotids are exposed and separated from the vagosympathetic nerve trunk. A loop of unwaxed dental floss (Johnson and Johnson) is placed around each carotid. The ends of the floss are each passed through one of the lumens of a double lumen catheter (Dural Plastics and Engineering, Dural, NSW, Australia). The catheter and dental floss are passed through the dorsal musculature and exited at the dorsal surface of the neck. The catheter is fixed in position, directly above the carotid artery, using cyanoacrylate adhesive at the exit site. The dental floss length is marked in order to assure that the animal does not occlude the carotid during daily cleaning and exploratory activity. The ventral incision is closed with 9 mm wound clips. After 48 hours following instrumentation, ischemia is produced by gently pulling the looped dental floss until the artery is occluded. Occlusion of the artery is associated with depression of spontaneous motor activity, loss of consciousness, ptosis and a change in breathing pattern. Complete interruption of blood flow occurs under these conditions. The occlusion is maintained for 5 minutes, and then the dental floss is removed to allow complete reperfusion, when these symptoms reverse. After reperfusion, the catheter is trimmed flush with the surface of the neck.

During the 5 minutes of ischemia and for a minimum of 2 hours after reversal of carotid occlusion, rectal and cranial temperature will be maintained at 36–37° in all animals. The rectal and cranial temperatures will be adjusted to the desired levels by heating or cooling from a blanket-jacketed water bath, as described previously (Busto, R., et al., *Stroke*, 20, 904–910, 1989; Campos-Gonzales, R., and Kindy, M. S., *J. Neurochem.*, 59, 1955–1958, 1992). All gerbils will be monitored for seizures that may occur during postischemic reperfusion. Any gerbil demonstrating motor activity that could be associated with seizures is discarded.

Gerbils (n=6) are pretreated intraperitoneally, 30 minutes prior to the initiation of carotid occlusion, with an appropriate dose of the triazoline or AAP compound. If the highest dose of any of the test compounds caused undue toxicity or mortality, then a lower dose of drug is used (eg. 100, 150, and 200 mg/kg). All animals are tested for postischemic locomotor activity using a computer-controlled monitoring equipment. A brief description of the equipment and the technique are as follows. The locomotor activity arena consists of a walled, cylindrical drum of 2-foot diameter that is equipped with two orthogonally placed photocell detector systems. Interruption of each of the photocell detector beams will define an activity count. All activity counts will be recorded automatically by an IBM computer system. Each gerbil will be tested 24 hours after reversal of carotid occlusion or sham-ischemia.

After locomotor activity testing, gerbils are evaluated for differences in patrolling behavior using a eight-arm radial maze. In this procedure, animals are placed into the center start chamber of the maze, the barrier removed and the amount of time and the number of times, the animals make an error recorded, prior to completion of exploration in all 8 arms of the maze. An error is defined as the revisiting of an arm by entering to the extent of the entire body without including tail by the animal. If the animal persevers or fails to leave the arm for longer than fifteen minutes, the session is terminated. In all the evaluations reported here, animals never exceeded the fifteen minute cut-off point and all eight-arms were successfully explored with differing degrees of errors. In the control population of the animals, the number of errors and exploration of the maze with no prior experience (naive) was approximately 5 errors. Data are expressed as the mean (+/-S.E) for groups of 6 gerbils. Following 5 minutes of bilateral carotid occlusion and testing at 24 hours, gerbils make an average number of errors of 28. When animals are pretreated with drug, there is a dose-related decrease in the number of errors made (Table IV). The threshold for protection in the maze test is lower than that seen in the locomotor activity test. While not significantly different from saline, a dose of 10 mg/kg slightly reduces the number of errors in post ischemic gerbils.

All animals will then be subjected to seven day post-reperfusion histopathological assessment after being re-anesthetized with 60 mg/kg of pentobarbital. Histopathology is determined using frozen sections fixed on treated slides and stained with hematoxylin-eosin for cell body counting. Changes in neuronal nuclei are determined for the dorsal hippocampus and for the CA3 region as comparison. Histopathological evaluation of gerbil brains seven days after 5 minutes of ischemia demonstrates, the expected loss of CA1 hippocampus pyramidal cells (Kirino, T., *Brain Res.*, 239, 57, 1982).

Table V presents the results of testing the compounds in the gerbil model. This table identifies the specific compounds tested by their chemical name, and provides the test model, the route of administration, and the antiischemic activity as indicated by neuronal density and radial maze errors and calculated as percent protection afforded by the compound, when administered intraperitoneally to the gerbils as a pretreatment dose.

EXAMPLE 6

MCAO Rat Model of Reversible Focal Cerebral Ischemia:

Males of a spontaneously hypertensive inbred strain of Wistar rat (SHR) (250–350 gm., purchased from Harlan, Indianapolis, Ind.) are used for the preparation of this model since they have been found superior to others in producing consistent infarct volumes and also because hypertension is a well-documented risk factor in stroke (Brint, S., et al., *J. Cereb. Blood Flow Metab.*, 8, 474–485, 1988). The rats are maintained under conditions of controlled lighting (12:12 light/dark cycle) and temperature (22° C.) and allowed free access to lab chow and tap water. All experiments are performed during "lights on" hours. A method of reversible focal ischemia in the rat is used, similar to the original technique of Brint and colleagues (1988) as modified by Aronowski and co-workers (Aronowski, J., et al., *Stroke*, 25, 2235–2240, (1994). It involves temporary occlusion of the MCA (middle cerebral artery) and ipsilateral CCA (common carotid artery) for two hours, to produce infarct volumes that are 50% of those observed with permanent CCA-MCA occlusion (Pettigrew, L. C., et al., *J. Cereb. Blood Flow Metab.*, 16, 1189–1202, 1996; Smith-Swintosky, V. L., et al., *J. Cereb. Blood Flow Metab.*, 16, 585–598, 1996).

Animals are fasted overnight prior to surgical preparation for ischemia. Each rat is anesthetized with 500 mg/kg chloral hydrate for isolation of MCA and CCA. A catheter is inserted into the right femoral artery for sampling of blood and measurement of mean arterial blood pressure (MABP) on a graphic recorder (Model RS3400, Gould Electronics, Centerville, Ohio), to monitor preischemic and 30 min postischemic blood glucose levels, blood gases and hematocrits. A second catheter is inserted into the right femoral vein for injection of drug or vehicle. Electroencephalographic (EEG) and electrocardiographic (ECG) activities are monitored through subdermal electrodes and displayed on the graphic recorder. Thermistor probes are inserted into the rectum and temporalis muscles to monitor body and brain temperature, which is maintained at 36–37° C. by external warming. The left CCA is isolated through an anterior incision in the neck. A second incision is made between the lateral canthus of the left eye and the ipsilateral external auditory canal to expose the underlying skull. Under direct visualization with a Zeiss operating microscope, the left MCA is exposed through a 2-mm burrhole drilled 2–3 mm rostral to the fusion of the zygomatic arch and the squamosal bone. The dura is opened with a sharp needle and an alloy wire (0.1 mm diameter) is inserted beneath the MCA just superior to the inferior cortical vein. The MCA is elevated from the cortical surface and reversibly occluded by compression against the wire. Obstruction of blood flow in the MCA is confirmed by direct microscopic observation. A bed of saline-soaked cotton is fashioned to keep the MCA moist while it is being occluded. A surgical clip is used to occlude the CCA for the two-hour period. Ischemia is reversed by removing the clip from the CCA and withdrawing the wire from beneath the MCA. The scalp and neck incisions are sutured before the rat is returned to its cage and given free access to water and chow.

Drug is administered intraperitoneally before ischemia or during postischemic reperfusion. The doses selected are those shown to be effective in preventing CA1 neuronal loss in pretreated gerbils. Groups of sham-ischemic (n=10) and ischemic control (n=10) animals are prepared for comparison to drug-treated SHRs. Other groups of sham-ischemic animals are pretreated with the most effective dose of each compound shown to prevent CA1 neuronal loss in gerbils (n=6 in each group). Another group of six SHRs will be pretreated with the same maximally effective dose of each neuroprotective compound before the animals undergo two hours of CCA-MCA occlusion. The post-treatment groups are given the same dose immediately after reversal of ischemia, or following one, three, or six hours of reperfusion (n=6 in each group). All animals will undergo functional assessment of cognitive performance before being euthanized for measurement of infarct volume 24 hours after reversal of ischemia.

Measurement of Infarct Volume:

The size of the infarction resulting from two hours of MCAO, is quantified using triphenyltetrazolium chloride (TTC) staining as described by Bederson, J. B., and colleagues (*Stroke,* 17, 1304–1308, 1986). Twenty-four hours following MCAO, rats are re-anesthetized with chloral hydrate (500 mg/kg body weight) and perfused transcardially with heparinized saline. The brains are removed and chilled at −20° C. for 15 minutes before being placed in a Rodent Brain Matrix (ASI Instruments). Seven serial one-mm thick coronal sections through the rostral to caudal extent of the infarction are obtained from each brain, beginning two mm from the frontal pole (corresponding to approximately 10.2 mm from the intra-aural line). This procedure reproducibly includes the entire infarction observed in permanent focal ischemia (Smith-Swintosky, V. L., et al., *J. Cereb. Blood Flow Metab.,* 16, 585–598, 1996). The individual sections are immersed in 2% TTC and incubated at 37° C. for 10 minutes on each surface. The TTC-stained sections are then placed in 10% formalin and kept in darkness at 4° C. for at least 24 hours. The infarct area in each section is determined with a computer-assisted image analysis system, consisting of a Power Macintosh computer (Apple Computer) equipped with a Quick Capture frame grabber card (Data Translations), Hitachi CCD camera mounted on an Olympus BX40 microscope, and NIH image Analysis software, v. 1.55. The system is calibrated against a Kodak Optical Density Standard. An optical density threshold is taken from healthy gray matter in the unaffected right cortex and used to create an artificial color image to distinguish between infarcted and normal tissue. The artificial color image and video photograph of each slice is used to compute the area of the infarct (38.4 pixels/mm), which is expressed as a fraction of the total area in the left hemisphere. The total volume of the infarction is computed by multiplying the infarct area in each coronal section by the number of slices (n=7) and the thickness of each slice (one mm uniformly). All measurements of infarct volume are performed by a single operator blinded to treatment status. Statistical comparison of the ischemic control animals to multiple groups of treated, ischemic rats will be accomplished by ANOVA with Dunnett's post hoc test.

TABLE I 1-(Phenyl)-5-(pyridyl)-$\Delta^2$-1,2,3-triazolines

| Compound | Melting Point, °C. | Yield, % |
|---|---|---|
| (1) 1-(Phenyl)-5-(4-pyridyl)-$\Delta^2$-1,2,3-triazoline | 160–161 | 68 |
| (2) 1-(p-Chlorophenyl)-5-(4-pyridyl)-$\Delta^2$-1,2,3-triazoline | 151–152 | 82 |
| (3) 1-(m-Chlorophenyl)-5-(4-pyridyl)-$\Delta^2$-1,2,3-triazoline | 109–111 | 80 |
| (4) 1-(p-Fluorophenyl)-5-(4-pyridyl)-$\Delta^2$-1,2,3-triazoline | 139–140 | 91 |
| (5) 1-(m-Fluorophenyl)-5-(4-pyridyl)-$\Delta^2$-1,2,3-triazoline | | |
| (6) 1-(p-Bromophenyl)-5-(4-pyridyl)-$\Delta^2$-1,2,3-triazoline | 158–160 | 51 |
| (7) 1-(m-Bromophenyl)-5-(4-pyridyl)-$\Delta^2$-1,2,3-triazoline | | |
| (8) 1-(3,4-Dichlorophenyl)-5-(4-pyridyl)-$\Delta^2$-1,2,3-triazoline | 171–172 | 82 |
| (9) 1-(3,5-Dichlorophenyl)-5-(4-pyridyl)-$\Delta^2$-1,2,3-triazoline | | |
| (10) 1-(p-Trifluoromethylphenyl)-5-(4-pyridyl)-$\Delta^2$-1,2,3-triazoline | 149–150 | 58 |
| (11) 1-(m-Trifluoromethylphenyl)-5-(4-pyridyl)-$\Delta^2$-1,2,3-triazoline | 68–71 | 42 |
| (12) 1-(p-Methylphenyl)-5-(4-pyridyl)-$\Delta^2$-1,2,3-triazoline | 157–158 | 97 |
| (13) 1-(m-Methylphenyl)-5-(4-pyridyl)-$\Delta^2$-1,2,3-triazoline | | |
| (14) 1-(p-Methoxyphenyl)-5-(4-pyridyl)-$\Delta^2$-1,2,3-triazoline | 148–148.5 | 45 |

TABLE I-continued 1-(Phenyl)-5-(pyridyl)-Δ²-1,2,3-triazolines

| | Compound | Melting Point, °C. | Yield, % |
|---|---|---|---|
| (15) | 1-(m-Methoxyphenyl)-5-(4-pyridyl)-Δ²-1,2,3-triazoline | | |
| (16) | 1-(3,4-Difluorophenyl)-5-(4-pyridyl)-Δ²-1,2,3-triazoline | | |
| (17) | 1-(Phenyl)-5-(3-pyridyl)-Δ²-1,2,3-triazoline | 113–114 | 27 |
| (18) | 1-(m-Chlorophenyl)-5-(3-pyridyl)-Δ²-1,2,3-triazoline | 75–77 | 75 |
| (19) | 1-(3,5-Dichlorophenyl)-5-(3-pyridyl)-Δ²-1,2,3-triazoline | 95–97 | 70 |
| (20) | 1-(p-Trifluoromethylphenyl)-5-(3-pyridyl)-Δ²-1,2,3-triazoline | 138–140 | 50 |
| (21) | 1-(m-Trifluoromethylphenyl)-5-(3-pyridyl)-Δ²-1,2,3-triazoline | 72–74 | 40 |
| (22) | 1-(p-Fluorophenyl)-5-(3-pyridyl)-Δ²-1,2,3-triazoline | 104–106 | 60 |
| (23) | 1-(m-Fluorophenyl)-5-(3-pyridyl)-Δ²-1,2,3-triazoline | | |
| (24) | 1-(m-Bromophenyl)-5-(3-pyridyl)-Δ²-1,2,3-triazoline | 75–77 | 65 |
| (25) | 1-(m-Methylphenyl)-5-(3-pyridyl)-Δ²-1,2,3-triazoline | | |
| (26) | 1-(m-Methoxyphenyl)-5-(3-pyridyl)-Δ²-1,2,3-triazoline | | |
| (27) | 1-(p-Chlorophenyl)-5-(2-pyridyl)-Δ²-1,2,3-triazoline | 138 | 80 |
| (28) | 1-(Phenyl)-5-(2-pyridyl)-Δ²-1,2,3-triazoline | 83–85 | 53 |
| (29) | 1-(p-Trifluoromethylphenyl)-5-(2-pyridyl)-Δ²-1,2,3-triazoline | | |

TABLE II 1-(Phenyl)-5-(2-oxo-1-pyrrolidino)-Δ²-1,2,3-triazolines

| | | Melting Point, °C. | Yield, % |
|---|---|---|---|
| (1) | 1-(Phenyl)-5-(2-oxo-1-pyrrolidino)-Δ²-1,2,3-triazoline | 118.5–121 | 46 |
| (2) | 1-(p-Chlorophenyl)-5-(2-oxo-1-pyrrolidino)-Δ²-1,2,3-triazoline | 126–128 | 62 |
| (3) | 1-(3,4-Dichlorophenyl)-5-(2-oxo-1-pyrrolidino)-Δ²-1,2,3-triazoline | 133–133.5 | 70 |
| (4) | 1-(p-Bromophenyl)-5-(2-oxo-1-pyrrolidino)-Δ²-1,2,3-triazoline | 129–131.5 | 60 |
| (5) | 1-(p-Fluorophenyl)-5-(2-oxo-1-pyrrolidino)-Δ²-1,2,3-triazoline | 111–114 | 21 |
| (6) | 1-(p-Trifluoromethylphenyl)-5-(2-oxo-1-pyrrolidino)-Δ²-1,2,3-triazoline | 130–133 | 66 |
| (7) | 1-(m-Trifluoromethylphenyl)-5-(2-oxo-1-pyrrolidino)-Δ²-1,2,3-triazoline | 102–105 | 60 |
| (8) | 1-(p-Methylphenyl)-5-(2-oxo-1-pyrrolidino)-Δ²-1,2,3-triazoline | 110.5–113 | 55 |
| (9) | 1-(p-Methoxyphenyl)-5-(2-oxo-1-pyrrolidino)-Δ²-1,2,3-triazoline | 122–125 | 62 |
| (10) | 1-(3,5-Dichlorophenyl)-5-(2-oxo-1-pyrrolidino)-Δ²-1,2,3-triazoline | | |
| (11) | 1-(m-Chlorophenyl)-5-(2-oxo-1-pyrrolidino)-Δ²-1,2,3-triazoline | | |

TABLE III

Aminoalkylpyridine (AAP) Compounds (Methyl, Ethyl or Propylamine Derivatives)

| | Compound | Melting Point, °C. | Yield, % |
|---|---|---|---|
| (1) | N-(Phenyl)-4-pyridylmethylamine | | |
| (2) | N-(p-Chlorophenyl)-4-pyridylmethylamine | 91–94 | 26 |
| (3) | N-(3,4-Dichlorophenyl)-4-pyridylmethylamine | 99–101.5 | 31 |
| (4) | N-(3,5-Dichlorophenyl)-4-pyridylmethylamine | | |
| (5) | N-(m-Chlorophenyl)-4-pyridylmethylamine | 82–84 | 18 |
| (6) | N-(p-Bromophenyl)-4-pyridylmethylamine | 92–94.5 | 32 |
| (7) | N-(m-Bromophenyl)-4-pyridylmethylamine | | |
| (8) | N-(p-Fluorophenyl)-4-pyridylmethylamine | 67–70 | 33 |
| (9) | N-(m-Fluorophenyl)-4-pyridylmethylamine | | |
| (10) | N-(p-Methylphenyl)-4-pyridylmethylamine | 71–73 | 38 |
| (11) | N-(p-Methoxyphenyl)-4-pyridylmethylamine | 74.5–76 | 33 |
| (12) | 1-[N-(p-Methylphenyl)]-1-(4-pyridyl)-1-ethylamine | 93–95.5 | 72 |
| (13) | 1-[N-(p-Methoxyphenyl)]-1-(4-pyridyl)-1-ethylamine | 74.5–76 | 70 |
| (14) | 1-[N-(Phenyl)]-1-(4-pyridyl)-1-ethylamine | 126–128 | 60 |
| (15) | 1-[N-(m-Chlorophenyl)]-1-(4-pyridyl)-1-ethylamine | 157–159.5 | 71 |
| (16) | 1-[N-(3,4-Dichlorophenyl)]-1-(4-pyridyl)-1-ethylamine | 153.5–155 | 54.3 |
| (17) | 1-[N-(3,5-Dichlorophenyl)]-1-(4-pyridyl)-1-ethylamine | 150–152.5 | 74 |
| (18) | 1-[N-(p-Bromophenyl)]-1-(4-pyridyl)-1-ethylamine | 107–108.5 | 62 |
| (19) | 1-[N-(m-Bromophenyl)]-1-(4-pyridyl)-1-ethylamine | | |
| (20) | 1-[N-(p-Fluorophenyl)]-1-(4-pyridyl)-1-ethylamine | 85–87 | 60 |
| (21) | 1-[N-(m-Fluorophenyl)]-1-(4-pyridyl)-1-ethylamine | | |
| (22) | 1-[N-(3,4-Difluorophenyl)]-1-(4-pyridyl)-1-ethylamine | 87–90.0 | 72 |
| (23) | 1-[N-(m-Trifluoromethylphenyl)]-1-(4-pyridyl)-1-ethylamine | 149–151 | 72 |
| (24) | 1-[N-(Phenyl)]-1-(3-pyridyl)-1-ethylamine | 132.5–134 | 77 |

TABLE III-continued

Aminoalkylpyridine (AAP) Compounds (Methyl, Ethyl or Propylamine Derivatives)

| | Compound | Melting Point, °C. | Yield, % |
|---|---|---|---|
| (25) | 1-[N-(m-Chlorophenyl)]-1-(3-pyridyl)-1-ethylamine | 120–122 | 47 |
| (26) | 1-[N-(p-Fluorophenyl)]-1-(3-pyridyl)-1-ethylamine | | |
| (27) | 1-[N-(m-Fluorophenyl)]-1-(3-pyridyl)-1-ethylamine | | |
| (28) | 1-[N-(p-Bromophenyl)]-1-(3-pyridyl)-1-ethylamine | 128.5–130.5 | 47 |
| (29) | 1-[N-(m-Bromophenyl)]-1-(3-pyridyl)-1-ethylamine | | |
| (30) | 1-[N-(p-Methylphenyl)]-1-(3-pyridyl)-1-ethylamine | 112–113.5 | 62 |
| (31) | 1-[N-(p-Methoxyphenyl)]-1-(3-pyridyl)-1-ethylamine | 73–74.5 | 6.3 |
| (32) | 1-[N-(3,4-Dichlorophenyl)]-1-(3-pyridyl)-1-ethylamine | 127–128.5 | 78 |
| (33) | 1-[N-(3,5-Dichlorophenyl)]-1-(3-pyridyl)-1-ethylamine | | |
| (34) | 1-[N-(Phenyl)]-1-(4-pyridyl)-1-propylamine | 75–78 | 82 |
| (35) | 1-[N-(p-Chlorophenyl)]-1-(4-pyridyl)-1-propylamine | 133–135 | 84 |
| (36) | 1-[N-(m-Chlorophenyl)]-1-(4-pyridyl)-1-propylamine | 127.5–129.5 | 54 |
| (37) | 1-[N-(p-Bromophenyl)]-1-(4-pyridyl)-1-propylamine | 128–130.5 | 74.5 |
| (38) | 1-[N-(m-Bromophenyl)]-1-(4-pyridyl)-1-propylamine | | |
| (39) | 1-[N-(p-Fluorophenyl)]-1-(4-pyridyl)-1-propylamine | 94.5–97 | 45.6 |
| (40) | 1-[N-(m-Fluorophenyl)]-1-(4-pyridyl)-1-propylamine | | |
| (41) | 1-[N-(3,4-Difluorophenyl)]-1-(4-pyridyl)-1-propylamine | 104–106.5 | 40 |
| (42) | 1-[N-(3,5-Difluorophenyl)]-1-(4-pyridyl)-1-propylamine | | |
| (43) | 1-[N-(p-Methoxyphenyl)]-1-(4-pyridyl)-1-propylamine | 86–88 | 62 |
| (44) | 1-[N-(p-Methylphenyl)]-1-(4-pyridyl)-1-propylamine | 117–119.5 | 74 |
| (45) | 1-[N-(m-Methoxyphenyl)]-1-(4-pyridyl)-1-propylamine | | |
| (46) | 1-[N-(m-Methylphenyl)]-1-(4-pyridyl)-1-propylamine | | |
| (47) | 1-[N-(3,4-Dichlorophenyl)]-1-(4-pyridyl)-1-propylamine | 154–156 | 31 |
| (48) | 1-[N-(3,5-Dichlorophenyl)]-1-(4-pyridyl)-1-propylamine | | |
| (49) | 1-[N-(Phenyl)]-1-(3-pyridyl)-1-propylamine | 90–92 | 39 |
| (50) | 1-[N-(p-Chlorophenyl)]-1-(3-pyridyl)-1-propylamine | | |
| (51) | 1-[N-(m-Chlorophenyl)]-1-(3-pyridyl)-1-propylamine | | |
| (52) | 1-[N-(p-Bromophenyl)]-1-(3-pyridyl)-1-propylamine | | |
| (53) | 1-[N-(m-Bromophenyl)]-1-(3-pyridyl)-1-propylamine | | |
| (54) | 1-[N-(p-Fluorophenyl)]-1-(3-pyridyl)-1-propylamine | | |
| (55) | 1-[N-(m-Fluorophenyl)]-1-(3-pyridyl)-1-propylamine | | |
| (56) | 1-[N-(3,4-Difluorophenyl)]-1-(3-pyridyl)-1-propylamine | | |
| (57) | 1-[N-(3,5-Difluorophenyl)]-1-(3-pyridyl)-1-propylamine | | |
| (58) | 1-[N-(p-Methylphenyl)]-1-(3-pyridyl)-1-propylamine | 100–104 | 32 |
| (59) | 1-[N-(m-Methylphenyl)-1-(3-pyridyl)]-1-propylamine | | |
| (60) | 1-[N-(p-Methoxyphenyl)]-1-(3-pyridyl)-1-propylamine | 94.5–96 | 74 |
| (61) | 1-[N-(m-Methoxyphenyl)]-1-(3-pyridyl)-1-propylamine | | |
| (62) | 1-[N-(3,4-Dichlorophenyl)]-1-(3-pyridyl)-1-propylamine | | |
| (63) | 1-[N-(3,5-Dichlorophenyl)]-1-(3-pyridyl)-1-propylamine | | |
| (64) | 1-[N-(Phenyl)]-1-(phenyl)-1-(4-pyridyl)methylamine | 91.5–94 | 48 |
| (65) | 1-[N-(p-Methoxyphenyl)]-1-(phenyl)-1-(4-pyridyl)-methylamine | 112–115 | 96.7 |
| (66) | 1-[N-(m-Methoxyphenyl)]-1-(phenyl)-1-(4-pyridyl)-methylamine | 121.5–123 | 98 |
| (67) | 1-[N-(p-Chlorophenyl)]-1-(phenyl)-1-(4-pyridyl)-methylamine | 135–137 | 71 |
| (68) | 1-[N-(m-Chlorophenyl)]-1-(phenyl)-1-(4-pyridyl)-methylamine | 104–106 | 49 |
| (69) | 1-[N-(p-Methylphenyl)]-1-(phenyl)-1-(4-pyridyl)-methylamine | 134–135.5 | 60 |
| (70) | 1-[N-3,5-Dichlorophenyl)]-1-(phenyl)-1-(4-pyridyl)-methylamine | Sublimes | 56 |
| (71) | 1-[N-(m-Trifluoromethylphenyl)]-1-(phenyl)-1-(4-pyridyl)-methylamine | 123–125.5 | 70 |
| (72) | 1-[N-(p-Bromophenyl)]-1-(phenyl)-1-(4-pyridyl)-methylamine | | |
| (73) | 1-[N-(p-Dimethylaminophenyl)]-1-(phenyl)-1-(4-pyridyl)-methylamine | 149–151 | 63 |
| (74) | 1-[N-(3,4-Dichlorophenyl)]-1-(phenyl)-1-(4-pyridyl)-methylamine | 130–132.5 | |
| (75) | 1-[N-(p-Chlorophenyl)]-1-(phenyl)-1-(3-pyridyl)-methylamine | 85–87 | 58 |
| (76) | 1-[N-(m-Chlorophenyl)]-1-(phenyl)-1-(3-pyridyl)-methylamine | 77–80 | |
| (77) | 1-[N-(p-Methylphenyl)]-1-(phenyl)-1-(3-pyridyl)-methylamine | 89.5–92.5 | 50 |
| (78) | 1-[N-(p-Methoxyphenyl)]-1-(phenyl)-1-(3-pyridyl)-methylamine | 114–116 | 68.5 |
| (79) | 1-[N-(Phenyl)]-1-(phenyl)-1-(3-pyridyl)methylamine | 113.5–115.5 | 66.8 |
| (80) | 1-[N-(3,4-Dichlorophenyl)]-1-(phenyl)-1-(3-pyridyl)-methylamine | 108.5–111 | 48 |
| (81) | 1-[N-(p-Bromophenyl)]-1-(phenyl)-1-(3-pyridyl)-methylamine | 114.5–17.5 | 22 |
| (82) | 1-[N-(m-Trifluoromethylphenyl)]-1-(phenyl)-1-(3-pyridyl)-methylamine | 81–83.5 | |

TABLE III-continued

Aminoalkylpyridine (AAP) Compounds (Methyl, Ethyl or Propylamine Derivatives)

| Compound | Melting Point, °C. | Yield, % |
|---|---|---|
| (83) 1-[N-(3,5-Dichlorophenyl)]-1-(phenyl)-1-(3-pyridyl)-methylamine | 93–95 | 17 |
| (84) 1-[N-(p-Chlorophenyl)]-1,1-(bis-2-pyridyl)methylamine | 117–119.5 | |

TABLE IV

Results of Testing 1,2,3-Triazolines and AAP Compounds in the Gerbil Model of Global Ischemia. Degree of Protection in Terms of Neuronal Cell Count and Number of Radial Arm Maze Errors at Three Different Drug Concentrations

| | Degree of Protection, % Test Concentrations, mg/kg | | | | | |
|---|---|---|---|---|---|---|
| | Neuronal Cell Count, %[a] | | | Radial Maze Error, %[b] | | |
| Compound | 100 | 150 | 200 | 100 | 150 | 200 |
| (1) 1-(Phenyl)-5-(4-pyridyl)-$\Delta^2$-1,2,3-triazoline | 83.0 | 91.4 | 96.5 | 28.9 | 31.6 | 27.4 |
| (2) 1-(p-Chlorophenyl)-5-(4-pyridyl)-$\Delta^2$-1,2,3-triazoline | 65.3 | 82.2 | 91.4 | 44.7 | 30.8 | 30.1 |
| (3) 1-(3,4-Dichlorophenyl)-5-(4-pyridyl)-$\Delta^2$-1,2,3-triazoline | 60.0 | 74.1 | 88.5 | 62.1 | — | — |
| (4) 1-(p-Fluorophenyl)-5-(4-pyridyl)-$\Delta^2$-1,2,3-triazoline | 54.9 | 67.8 | 77.3 | 72.2 | 58.3 | 45.9 |
| (5) 1-(p-Trifluoromethylphenyl)-5-(4-pyridyl)-$\Delta^2$-1,2,3-triazoline | 47.0 | 46.5 | 62.5 | 75.9 | — | — |
| (6) 1-(m-Chlorophenyl)-5-(4-pyridyl)-$\Delta^2$-1,2,3-triazoline | 60.1 | 71.2 | 87.4 | 44.7 | 25.7 | 21.3 |
| (7) 1-(p-Bromophenyl)-5-(4-pyridyl)-$\Delta^2$-1,2,3-triazoline | 25.6 | 39.5 | 47.9 | 73.5 | 61.7 | 54.2 |
| (8) 1-(3,5-Dichlorophenyl)-5-(4-pyridyl)-$\Delta^2$-1,2,3-triazoline | 30.6 | 41.3 | 49.8 | 72.2 | 56.6 | 48.1 |
| (9) 1-(p-Chlorophenyl)-5-(3-pyridyl)-$\Delta^2$-1,2,3-triazoline | 47.9 | 53.7 | 59.7 | 58.7 | 52.3 | 45.3 |
| (10) 1-(m-Chlorophenyl)-5-(3-pyridyl)-$\Delta^2$-1,2,3-triazoline | 46.8 | 47.3 | 62.8 | 60.3 | 59.0 | 45.7 |
| (11) 1-(Phenyl)-5-(3-pyridyl)-$\Delta^2$-1,2,3-triazoline | 49.5 | 55.6 | 61.0 | 57.0 | 52.0 | 44.3 |
| (12) 1-(p-Chlorophenyl)-5-(2-pyridyl)-$\Delta^2$-1,2,3-triazoline | 45.6 | 36.9 | 63.5 | 60.7 | 58.3 | 42.7 |
| (13) 1-(p-Bromophenyl)-5-(2-pyridyl)-$\Delta^2$-1,2,3-triazoline | 47.6 | 47.2 | 62.5 | 62.7 | 60.0 | 39.7 |
| (14) 1-(Phenyl)-5-(2-oxo-1-pyrrolidino)-$\Delta^2$-1,2,3-triazoline | 22.0 | 29.9 | 38.5 | 82.7 | 70.2 | 60.7 |
| (15) 1-(p-Chlorophenyl)-5-(2-oxo-1-pyrrolidino)-$\Delta^2$-1,2,3-triazoline | 29.9 | 33.9 | 45.2 | 71.9 | 57.6 | 54.9 |
| (16) 1-(p-Trifluoromethylphenyl)-(2-oxo-1-pyrrolidino)-$\Delta^2$-1,2,3-triazoline | 534.2 | 52.8 | 66.3 | 67.4 | 48.8 | 34.9 |
| (17) 1-(m-Trifluoromethylphenyl)-5-(2-oxo-1-pyrrolidino)-$\Delta^2$-1,2,3-triazoline | 25.8 | 38.2 | 45.8 | 76.3 | 63.4 | 52.2 |
| (18) 1-(p-Bromophenyl)-5-(2-oxo-1-pyrrolidino)-$\Delta^2$-1,2,3-triazoline | 6.4 | 17.2 | 21.4 | 82.2 | 76.2 | 74.1 |
| (19) 1-(p-Fluorophenyl)-5-(2-oxo-1-pyrrolidino)-$\Delta^2$-1,2,3-triazoline | 5.5 | 16.2 | 15.4 | 97.2 | 76.6 | 75.9 |
| (20) 1-(3,4-Dichlorophenyl)-5-(2-oxo-1-pyrrolidino)-$\Delta^2$-1,2,3-triazoline | 8.1 | 17.2 | 18.0 | 90.9 | 78.3 | 80.8 |
| (21) 1-(3,4-Dichlorophenyl)-5-[N-methyl)-N-acetamide] | 8.7 | 15.8 | 22.8 | 89.9 | 83.6 | 78.0 |
| (22) 1-[N-(p-Chlorophenyl)]-1-(4-pyridyl)-1-ethylamine) | 0 (No effect) | 6.6 | 14.5 | 100 (No effect) | 88.5 | 82.4 |
| (23) 1-[N-(p-Bromophenyl)]-1-(4-pyridyl)-1-ethylamine) | 0 (no effect) | 15.6 | 28.1 | 100 (no effect) | 81.2 | 71.3 |
| (24) 1-[N-(3,4,-Dichlorophenyl)]-1-(4-pyridyl)-1-ethylamine) | 26.4 | 32.9 | 45.2 | 74.7 | 66.3 | 65.1 |
| (25) 1-[N-(3-Chlorophenyl)]-1-(4-pyridyl)-1-ethylamine) | 29.6 | 39.6 | 38.9 | 82.6 | 77.6 | 82.2 |

TABLE IV-continued

Results of Testing 1,2,3-Triazolines and AAP Compounds in the Gerbil Model of Global Ischemia. Degree of Protection in Terms of Neuronal Cell Count and Number of Radial Arm Maze Errors at Three Different Drug Concentrations

| | Degree of Protection, % Test Concentrations, mg/kg | | | | | |
|---|---|---|---|---|---|---|
| | Neuronal Cell Count, %[a] | | | Radial Maze Error, %[b] | | |
| Compound | 100 | 150 | 200 | 100 | 150 | 200 |
| (26) 1-[N-(3,5,-Dichlorophenyl)]-1-(4-pyridyl)-1-ethylamine) | 29.7 | 32.7 | 44.1 | 87.1 | 84.5 | 72.7 |
| (27) 1-[N-(3-Trifluoromethylphenyl)]-1-(4-pyridyl)-1-ethylamine) | 15.1 | 14.6 | 11.7 | 103.8 | 109.1 | 111.0 |
| | (compound has no protective effect) | | | | | |
| (28) 1-[N-(p-methylphenyl)]-1-(4-pyridyl)-1-ethylamine) | 20.0 | 30.3 | 38.7 | 98.1 | 89.4 | 79.5 |
| (29) 1-[N-(p-Chlorophenyl)]-1-(3-pyridyl)-1-ethylamine) | 32.0 | 36.2 | 40.5 | 84.5 | 83.3 | 76.9 |
| (30) 1-[N-(3,4-dichlorophenyl)]-1-(3-pyridyl)-1-ethylamine) | 33.5 | 41.6 | 42.9 | 80.3 | 74.6 | 73.5 |
| (31) 1-[N-(p-Bromophenyl)]-1-(3-pyridyl)-1-ethylamine) | 35.7 | 19.7 | 6 | 81.8 | 101.1 | 114.0 |
| (32) (+)1-[N-(p-Chlorophenyl)]-1-(4-pyridyl)-1-1ethylamine) | 10.7 | 14.8 | 19.1 | 98.6 | 92.6 | 91.2 |
| (33) (−)1-[N-(p-Chlorophenyl)]-1-(4-pyridyl)-1-ethylamine) | 7.6 | 15.0 | 16.5 | 97.5 | 81.1 | 79.0 |

[a]Neuronal cell count is directly proportional to the surviving cells and is a measure of the degree of protection afforded by the drug.
[b]The smaller the percentage of errors, the better the protection afforded by drug. The maze errors are indirectly proportional to the neuronal cell count.

TABLE V

Results of Testing $\Delta^2$-1,2,3-Triazolines in the Rat Model of Focal Ischemia. Degree of Protection in Terms of Reduction in Infarct Volume; Ip Injection 30 min Prior to Ischemia, at 100, 150 and 200 mg/kg Dose

| | Reduction in Infarct Volume, % Test Concentrations of Drug, Dissolved in 0.5% Carboxymethyl Cellulose, mg/kg | | |
|---|---|---|---|
| Compound | 100 | 150 | 200 |
| (1) 1-(Phenyl)-5-(4-pyridyl)-$\Delta^2$-1,2,3-triazoline | 53.8 | 33.3 | 15.2 |
| (2) 1-(p-Chlorophenyl)-5-(4-pyridyl)-$\Delta^2$-1,2,3-triazoline | 16.9 | — | — |
| (3) 1-(p-Fluorophenyl)-5-(4-pyridyl)-$\Delta^2$-1,2,3-triazoline | 0 | — | — |
| | (No reduction in infarct volume) | | |

The invention has been described herein with reference to certain preferred embodiments. However, as obvious variations thereon will become apparent to those of skill in the art, the invention is not considered to be limited thereto.

TABLE VI

Results of Testing $\Delta^2$-1,2,3-Triazolines in the Rat Model of Focal Ischemia. Degree of Protection in Terms of Reduction in Infarct Volume; Post-Ischemic Ip Injection of Drug, Three Times, at the Beginning, then 1 hr. and 2 hrs. of Reperfusion. Ischemic Controls Treated 3 Times with Vehicle

| Compound | Reduction in Infarct Volume When Drug is Administered Ip Three Times, Postischemic, % |
|---|---|
| (1) 1-(p-Fluorophenyl)-5-(4-pyridyl)-$\Delta^2$-1,2,3-triazoline | 30 |
| (2) 1-(3,4-Dichlorophenyl)-5-(4-pyridyl)-$\Delta^2$-1,2,3-triazoline (25 mg/kg × 3) | 34 |
| (50 mg/kg × 3) | |

What is claimed is:

1. A non-neurotoxic antiischemic composition for the treatment of stroke in mammals, comprising as the active ingredient, an effective amount comprising from about 0.01 to about 99 wt. % of an antiischemic $\Delta^2$-1,2,3-triazoline compound, selected from the compounds of the formulae,

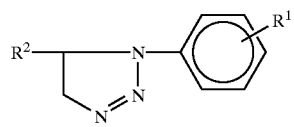

wherein $R^2$ is 4-pyridyl, 3-pyridyl, or 2-pyridyl and $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen, and a pharmaceutical carrier.

2. A composition according to claim 1 wherein $R^2$ is 4-pyridyl and $R^1$ is hydrogen.

3. A composition according to claim 1 wherein $R^2$ is 4-pyridyl and $R^1$ is p-chloro.

4. A composition according to claim 1 wherein $R^2$ is 4-pyridyl and $R^1$ is 3,4-dichloro.

5. A composition according to claim 1 wherein $R^2$ is 4-pyridyl and $R^1$ is p-fluoro.

6. A composition according to claim 1 wherein $R^2$ is 4-pyridyl and $R^1$ is p-trifluoromethyl.

7. A composition according to claim 1 wherein $R^2$ is 4-pyridyl and $R^1$ is m-chloro.

8. A composition according to claim 1 wherein $R^2$ is 4-pyridyl and $R^1$ is p-bromo.

9. A composition according to claim 1 wherein $R^2$ is 4-pyridyl and $R^1$ is 3,5-dichloro.

10. A composition according to claim 1 wherein $R^2$ is 3-pyridyl and $R^1$ is m-chloro.

11. A composition according to claim 1 wherein $R^2$ is 3-pyridyl and $R^1$ is p-chloro.

12. A composition according to claim 1 wherein $R^2$ is 3-pyridyl and $R^1$ is hydrogen.

13. A composition according to claim 1 wherein $R^2$ is 2-pyridyl and $R^1$ is p-bromo.

14. A composition according to claim 1 wherein $R^2$ is 2-pyridyl and $R^1$ is p-chloro.

15. A composition according to claim 1, wherein a sufficient amount of the antiischemic triazoline compound is contained in said composition to provide a dosage amount for mammal delivery ranging from about 25 mg to 200 mg per kg of body weight.

16. A composition according to claim 1, wherein the composition contains about 10–60 wt. % of the active ingredient.

17. A method for the treatment of cerebral ischemia resulting from stroke in mammals which comprises administration thereto of an effective dosage amount of a triazoline antiischemic composition selected from those of the following formula:

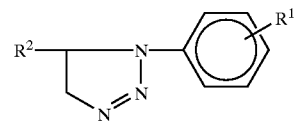

wherein $R^2$ is 4-pyridyl, 3-pyridyl, or 2-pyridyl and $R^1$ is 3,4- or 3,5-dichloro, p- or m-chloro, p- or m-bromo, p- or m-fluoro, p- or m-trifluoromethyl, p- or m-lower alkyl, p- or m-lower alkoxy or hydrogen, and a pharmaceutical carrier.

18. A method according to claim 17, wherein $R^2$ is 4-pyridyl and $R^1$ is hydrogen.

19. A method according to claim 17, wherein $R^2$ is 4-pyridyl and $R^1$ is p-chloro.

20. A method according to claim 17, wherein $R^2$ is 4-pyridyl and $R^1$ is 3,4-dichloro.

21. A method according to claim 17, wherein $R^2$ is 4-pyridyl and $R^1$ is p-fluoro.

22. A method according to claim 17, wherein $R^2$ is 4-pyridyl and $R^1$ is p-trifluoromethyl.

23. A method according to claim 17, wherein $R^2$ is 4-pyridyl and $R^1$ is m-chloro.

24. A method according to claim 17, wherein $R^2$ is 4-pyridyl and $R^1$ is p-bromo.

25. A method according to claim 17, wherein $R^2$ is 4-pyridyl and $R^1$ is 3,5-dichloro.

26. A method according to claim 17, wherein $R^2$ is 3-pyridyl and $R^1$ is m-chloro.

27. A method according to claim 17, wherein $R^2$ is 3-pyridyl and $R^1$ is p-chloro.

28. A method according to claim 17, wherein R is 3-pyridyl and $R^1$ is hydrogen.

29. A method according to claim 17, wherein $R^2$ is 2-pyridyl and $R^1$ is p-bromo.

30. A method according to claim 17, wherein $R^2$ is 2-pyridyl and $R^1$ is p-chloro.

31. A method according to claim 17, wherein the effective dosage amount ranges from about 25 mg to 200 mg per kg of mammal weight and administered four times daily.

* * * * *